US00RE38325E

(19) United States
(12) Reissued Patent
Krafft

(10) Patent Number: US RE38,325 E
(45) Date of Reissued Patent: Nov. 18, 2003

(54) METHOD FOR THE PRODUCTION OF TETRAKIS (PENTAFLUOROPHENYL) BORATES

(75) Inventor: Terry E. Krafft, Longmont, CO (US)

(73) Assignee: Boulder Scientific Company, Mead, CO (US)

(21) Appl. No.: 10/050,869

(22) Filed: Jan. 18, 2002

Related U.S. Patent Documents

Reissue of:
(64) Patent No.: 6,096,928
Issued: Aug. 1, 2000
Appl. No.: 09/353,156
Filed: Jul. 14, 1999

U.S. Applications:

(63) Continuation-in-part of application No. 09/077,999, filed as application No. PCT/US96/16390 on Oct. 15, 1996, now a bandoned.

(51) Int. Cl.[7] ..... C07F 5/02
(52) U.S. Cl. ..... 568/6
(58) Field of Search ..... 568/6

(56) References Cited

U.S. PATENT DOCUMENTS 5,488,169 A * 1/1996 Ikeda et al. ..... 568/3
5,600,005 A * 2/1997 Naganuma et al. ..... 568/6

* cited by examiner

*Primary Examiner*—Fiona T. Powers
(74) *Attorney, Agent, or Firm*—Edward S. Irons

(57) ABSTRACT

A process for preparing tetrakis (pentafluorophenyl) borate is described that involves reaction of a pentafluorophenyl magnesium halide with an alkali metal tetrafluoroborate.

6 Claims, No Drawings

METHOD FOR THE PRODUCTION OF TETRAKIS (PENTAFLUOROPHENYL) BORATES

Matter enclosed in heavy brackets [ ] appears in the original patent but forms no part of this reissue specification; matter printed in italics indicates the additions made by reissue.

This application is a continuation-in-part of Ser. No. 09/077,999 filed Jun. 15, 1998, now abandoned, which is the 35 U.S.C. §371 counterpart of application PCT/U.S.96/16390 filed Oct. 15, 1996.

FIELD OF THE INVENTION

This invention relates to the synthesis of tetrakis (pentafluorophenyl) borates by reaction of a tetrafluoroborate salt with a pentafluorophenyl compound.

BACKGROUND OF THE INVENTION

It is known to produce tetrakis (pentafluorophenyl) borates by reaction of boron trihalide with pentafluorophenyl lithium or pentafluorophenyl magnesium halide and by reaction of tris (pentafluorophenyl) boron with pentafluorophenyl lithium. See generally, published European patent application No. 0 604 961 A2 and U.S. Pat. No. 5,473,036. Such borates are important intermediates in the synthesis of catalysts used in combination with metallocene polymerization catalysts.

SUMMARY OF THE INVENTION

The invention provides a method for the production of tetrakis (pentafluorophenyl) borates by reacting a tetrafluoroborate salt with pentafluorophenyl magnesium halide in a non-interfering solvent.

DETAILED DESCRIPTION OF THE INVENTION

Pentafluorophenyl magnesium halides (Grignards) are known. See, e.g., Respess, et al., J. Organometal. Chem. (1969) 18:263–274 and Respess, et al., J. Organometal. Chem. (1969) 19:191–195. Pentafluorophenyl magnesium halides useful in the invention have the formula $C_6F_6MgX$ in which X is a halogen, e.g., iodine, chlorine or bromine, preferably bromine.

Tetrafluoroborate salts useful in the invention have the formula $QBF_4$ in which Q is sodium, lithium or potassium, preferably sodium.

The reaction between the Grignard and the tetrafluoroborate salt may be conducted in any non-interfering solvent. Typical solvents have the formula R—O—R' in which the R and R' are the same or different aliphatic hydrocarbon groups having 2–10 carbon atoms. Ethyl ether is preferred. The reaction is appropriately conducted at a temperature of 0° C. to 100° C., preferably at 30° C. to 35° C.

The tetrafluoroborate salt is added to the Grignard solution in stoichiometric amounts or in such greater or lesser amount as may be deemed appropriate. [In the preferred practice of the invention the tetrafluoroborate salt is added in an amount more than 15% of stoichiometric.] Preferably the reaction mixture is refluxed to expedite the reaction.

EXEMPLIFICATION OF THE INVENTION

EXAMPLE I

A reaction vessel is changed with 0.25 mol of $C_6H_5MgBr$ and 0.056 mol of $NaBF_4$ in an ethyl ether solvent. The reaction mixture is refluxed overnight under nitrogen. The reaction mixture was processed to recover 24.4 g of brown solids. Apparent yield 62.1%.

$^{19}F$ NMR peaks established the presence of tetrakis (pentafluorophenyl) borate in an amount corresponding to approximately 50% of the total product of the reaction.

EXAMPLE II

Example I was repeated using $NaBF_4$ ground by pestle and mortar and a 36 hour reflux time. Yield: 62.2% of a product having a tetrakis (pentafluorophenyl) borate purity of about 60% as indicated by $^{19}F$ NMR.

I claim:

1. A method for the production of tetrakis (pentafluorophenyl) borate which comprises reacting a pentafluorophenyl compound having the formula $C_6F_5MgX$ in which X is a halide with an alkali metal salt of tetrafluoroborate in a non-interfering solvent.

2. The claim 1 method in which the pentafluorophenyl compound is $C_6F_5MgBr$ and said alkali metal salt is $NaBF_4$.

3. The claim 1 or claim 2 method in which said solvent has the formula R—O—R' in which R and R' are the same or different aliphatic hydrocarbon groups having 2 to 10 carbon atoms.

4. The claim 1 or claim 2 method in which said solvent is ethyl ether.

5. A method which comprises reacting a compound having the formula $C_6F_5MgX$ in which X is a halide with a compound having the formula $QBF_4$ in which Q is sodium, lithium or potassium, said reaction being conducted at a temperature of 0° C. to 100° C. in a solvent being the formula R—O—R' in which R and R' are the same or different aliphatic hydrocarbon groups having 2 to 10 carbon atoms to produce a reaction mixture containing a tetrakis (pentafluorophenyl) borate and recovering said tetrakis (pentafluorophenyl) borate from said reaction mixture.

6. The claim 5 method in which $C_6H_5MgBr$ is reacted with $NaBF_4$ in ethyl ether.

[7. The claim 5 method in which the compound having the formula $C_6H_5MgX$ and compound $QBF_4$ are reacted in an amount which is more than 15% of the stoichiometric amount.]

* * * * *